United States Patent [19]

Hechenbleikner et al.

[11] 4,411,842

[45] Oct. 25, 1983

[54] OXIDATION OF ALKYL PHOSPHONOUS DICHLORIDES

[75] Inventors: Ingenuin Hechenbleikner, West Cornwall; William P. Enlow, Falls Village, both of Conn.

[73] Assignee: Borg-Warner Chemicals, Inc., Parkersburg, W. Va.

[21] Appl. No.: 321,857

[22] Filed: Nov. 16, 1981

[51] Int. Cl.$^3$ ................................................ C07F 9/42
[52] U.S. Cl. .................................................... 260/543 P
[58] Field of Search .................................... 260/543 P

[56] References Cited

U.S. PATENT DOCUMENTS 2,683,168  7/1954  Jensen et al. .................... 260/543
3,188,281  6/1965  Briggeman et al. ................ 202/40
3,210,418  10/1965  Pianfetti ........................ 260/543

OTHER PUBLICATIONS

Pianfetti, John A. et al. *J. Am. Chem. Society*, vol. 84 (1962) pp. 851–854.
Mellor, J. W. *Inorganic and Theoretical Chemistry*, vol. VIII (1949) pp. 810–811 and 1000–1002 Longmans, Publ.
Roberts, John D. et al. *Basic Principles of Organic Chemistry*, (1973) p. 1201 Calif. Inst. of Technology, Publ.
Gladshtein, B. M. et al. *Chemical Abstracts* (1961) vol. 55 #6375.

*Primary Examiner*—Natalie Trousof
*Assistant Examiner*—L. Hendriksen
*Attorney, Agent, or Firm*—Joseph Shekleton

[57] ABSTRACT

A method for converting methylphosphonous dichlorides to methyl phosphonic dichlorides.

4 Claims, No Drawings

OXIDATION OF ALKYL PHOSPHONOUS DICHLORIDES

This invention relates to a chemical process wherein improved yields of an oxidation product are obtained from methylphosphonous dichloride. Still more particularly, it relates to a process for the preparation of methylphosphonyl dichloride, as follows:

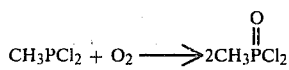

BACKGROUND OF THE INVENTION

Methylphosphonyl dichloride is useful as an intermediate in the preparation of dimethyl pentaerythritol diphosphonate which is in turn useful as a flame-retardant. U.S. Pat. No. 4,154,721 (Valdiserri et al.) shows the use of this compound in combination with a wide variety of halogenated organic compounds to impart a high degree of flame retardancy to polypropylene, ABS resins and polystyrene. Its preparation can be accomplished by reaction of the methyl phosphonyl dichloride of this invention with pentaerythritol in accordance with the equation:

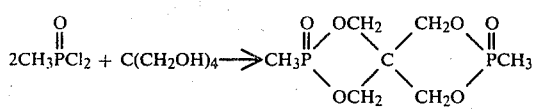

The preparation of phosphonyl dichlorides has been accomplished in the past by a number of different processes none of which have proved to be economically satisfactory. These are shown in Kosolapoff's "Organophosphorus Compounds", New York, Wiley (1950), at pages 61–63. Thus, the action of phosphorus pentachloride on the corresponding phosphonic acid yields the phosphonyl dichloride.

Another process, applicable to the preparation of phenylphosphonyl dichloride, involves the reaction of acetic acid and phenyl phosphorus tetrachloride.

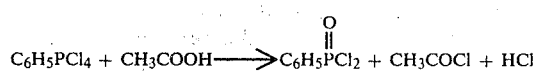

Esters of phosphonic acid likewise can be made to yield phosphonyl chlorides, by reaction with phosphorus pentachloride.

Still another method has involved oxidation of phenyldichlorophosphine ($C_6H_5PCl_2$) with oxygen (or air). Unfortunately, this method is somewhat hazardous unless all traces of free phosphorus are absent, and rather drastic conditions of time and temperature are required. Moreover, yields are low.

U.S. Pat. No. 3,188,281 (Briggeman et al.) shows the preparation of methylphosphonyl dichloride ("methyl dichlorophosphine oxide") by the phosgenation (with phosgene) of "pyro mix", a complex reaction mixture obtained in turn from the reaction of methanol and phosphorus trichloride.

All of the above methods of preparation, however, are fraught with disadvantages in the form of poor yields, inconvenient reaction conditions, etc. No convenient method for the preparation of this simple compound in good yields seems to have been available.

U.S. Pat. No. 2,683,168 (Jensen et al.) shows the reaction of an organic compound with phosphorus trichloride and oxygen to form a phosphonyl dichloride. The organic compound must contain an aliphatic carbon atom which is bonded only to carbon and hydrogen atoms and it must be free of sulfur and selenium. Such organic compounds can include hydrocarbons, chlorinated hydrocarbons, ethers, esters, ketones, etc., but apparently not methane or ethane.

U.S. Pat. No. 3,210,418 (Pianfetti) shows the preparation of aliphatic dichlorophosphines such as methyl dichlorophosphine by the reaction of methane and phosphorus trichloride. The reaction is catalyzed by a homogeneous, gaseous catalyst such as oxygen, a halogen, nitrogen oxides, etc. The reaction is carried out at high temperatures, e.g., 575° C.

"Formation of Phosphonous Dichlorides by Alkylation of Phosphorus Trichloride with Methane or Ethane" by Pianfetti et al., J. Am. Chem. Soc., 84, 851–854 (1962), shows much the same subject matter as the above Pianfetti patent.

SUMMARY OF THE INVENTION

The invention of this application is a method for preparing methylphosphonyl dichloride comprising contacting a mixture of methylphosphonous dichloride and phosphorus trichloride with oxygen so as to oxidize the methylphosphonous dichloride but leave substantially all of the phosphorus trichloride unoxidized, and distilling the resulting product mixture to obtain the desired methylphosphonyl dichloride.

An important advantage of this method is the fact that the unreacted phosphorus trichloride from the preparation of the starting methylphosphonous dichloride is made available for re-cycling in the overall process. Moreover, there is a saving of oxygen which would otherwise be used to oxidize this phosphorus trichloride.

The method requires no unusual conditions of temperature or pressure, the reaction is slightly exothermic and, on a small, laboratory scale, may be carried out most conveniently at temperatures within the range of from about −10° C. to about 60° C.

Ordinarily, because of the exothermic nature of the reaction no heat is supplied. In fact, when carried out on a large scale it is necessary to cool the reaction mixture externally to maintain a satisfactory and uniform temperature.

The oxygen may be used as such or it may be diluted with some inert gas. Dry air, for example, may be used. The oxygen simply is bubbled into the reaction mixture which is thus agitated to provide uniform temperature and a relatively homogeneous medium.

The reaction is continued until no more oxygen is consumed. The termination of the reaction may be checked by titrating a sample with iodine to assure the disappearance of all methylphosphonous chloride. The phosphorus trichloride remains unoxidized under the conditions of the reaction.

The mixture of methylphosphonous dichloride and phosphorus trichloride used in the process is that resulting from the reaction of methane and phosphorus trichloride, ordinarily in the presence of catalytic proportions of oxygen and at temperatures of from about 500° F. to about 650° F. This is the reaction taught by the Pianfetti patent above and its disclosure is incorporated herein by reference. The composition of such a mixture ranges from about 5% to about 25% of methylphosphonous dichloride and from about 75% to about 90% of phosphorus trichloride. The reaction is carried out conveniently by passing methane through a calibrated rotameter and then bubbling it through phosphorus trichloride. To the resulting gaseous mixture of methane and phosphorus trichloride there is added a catalytic amount of oxygen (or air) and this resulting mixture then is passed through a hot (550°-600° C.) tube. The product usually is distilled and the distillate is a mixture of methylphosphonous dichloride and phosphorus trichloride. The proportion of desired product (methylphosphonous dichloride) in this mixture is determined from a consideration of the mixture's density and referral to a calibration curve based in turn on the densities of these components.

The two components of this product mixture, viz., phosphorus trichloride and methylphosphonous dichloride, boil so close to one another, i.e., 76° C. and 82° C., that it is not practical to separate them for the purposes of preparing methylphosphonyl dichloride. Their oxidation products, however, viz., phosphorus oxychloride and methylphosphonyl chloride, are easily separable by fractionation. So also is a mixture of phosphorus trichloride and methylphosphonyl chloride and an important feature of the process of the present invention is the fact that it makes available just such a mixture. This fact permits the unoxidized phosphorus trichloride to be recycled for reaction with methane to produce additional methylphosphonous dichloride.

A solvent may be used in the method of the invention but ordinarily the method is carried out without a solvent. Suitable solvents include carbon tetrachloride, chloroform, tetrachloroethane, chlorobenzene and the like.

The method of the invention is illustrated in some detail in the following examples.

EXAMPLE 1

Methane is bubbled through 450 g. of phosphorus trichloride for seven hours at the rate of 500 cc./min. The mixed methane-phosphorus trichloride effluent is diluted with air (9 cc./min.) and then fed into a hot tube at 550°-600° C. A total of 313.5 g. of phosphorus trichloride is used. The liquid product weighs 252 g. Distillation yields 245.6 g. containing 49 g. of methylphosphonous.

EXAMPLE 2

The procedure of Example 1 is followed except that a total of 1660 g. of phosphorus trichloride is swept into the hot tube reactor by the combined methane and air. The liquid product, containing a small proportion of yellow, gummy solid, is shown (by its density, viz., 1.528) to contain 17% of methylphosphonous dichloride and 83% of phosphorus trichloride. Distillation yields 1474.5 g. of clear liquid.

EXAMPLE 3

The clear liquid product (1474.5 g.) obtained as in Example 2 is treated at 30° C. with oxygen at a rate commensurate with its absorption by the liquid. The temperature of the reaction mixture is maintained at about 30° C. by means of an ice-water bath. When no more oxygen is absorbed, and gas chromatographic (GC) analysis reflects the disappearance of substantially all the methylphosphonous dichloride, the introduction of oxygen is halted and the product mixture is distilled through a 45-cm., silver-lined column packed with Raschig rings. The unreacted phosphorus trichloride is removed at 76°-105° C. A second fraction is collected distilling at 35°-87° C./50 mm.; it weighs 255 g. (100% of the theory) and is identified as the desired methylphosphonyl dichloride by gas chromatography.

All parts and percentages herein unless otherwise expressly stated, are by weight.

We claim:

1. A method for preparing methylphosphonyl dichloride comprising contacting a mixture of from about 5% to about 25% of methylphosphonous dichloride and from about 75% to about 90% of phosphorus trichloride, at a temperature of from about −10° C. to about 60° C., with oxygen so as to oxidize the methylphosphonous dichloride but leave substantially all of the phosphorus trichloride unoxidized, and distilling the resulting product mixture to obtain the desired methylphosphonyl dichloride.

2. The method of claim 1 wherein the oxygen is introduced beneath the surface of the mixture.

3. The method of claim 1 wherein the mixture of methylphosphonous dichloride and phosphorus trichloride is obtained by reacting methane with phosphorus trichloride.

4. The method of claim 3 wherein the reaction of methane and phosphorus trichloride is carried out at a temperature within the range of 500°-650° C.

* * * * *